United States Patent [19]
Klein

[11] Patent Number: 4,775,116
[45] Date of Patent: Oct. 4, 1988

[54] CONTROL OF CRAFT UNDER HIGH-G PILOT STRESS

[76] Inventor: David S. Klein, 402 E. Beverley St., Staunton, Va. 24401

[21] Appl. No.: 902,975

[22] Filed: Sep. 2, 1986

[51] Int. Cl.⁴ .............................................. B64C 13/16
[52] U.S. Cl. .................... 244/76 R; 340/945
[58] Field of Search ..................... 244/76 R, 194, 196, 244/197; 340/945, 965; 128/1 A, 633, 634, 664, 665, 666; 180/272; 191/1 R

[56] References Cited

U.S. PATENT DOCUMENTS 2,414,747  1/1947  Kirschbaum ........................ 128/633
2,852,213  9/1958  Lambert et al. .................... 244/194

Primary Examiner—Galen Barefoot
Assistant Examiner—Rodney Corl
Attorney, Agent, or Firm—Michael Masnik

[57] ABSTRACT

Monitoring a pilot's oxygenation during flight using near infrared technology to detect pilot blackout, as for example during high G aircraft maneuvers. Initiating automatic programmed flight control or remote controller programmed flight control to avert loss of life, property or aircraft as a consequence of such detection.

19 Claims, 2 Drawing Sheets

CONTROL OF CRAFT UNDER HIGH-G PILOT STRESS

Field of the invention

This invention relates, in general, to monitoring the oxygenation of personnel carried aboard a moving craft for purposes of early detection of hypoxia approaching loss of consciousness and thereupon enabling appropriate craft control intervention to avert harm to personnell or property. The invention has particular application under conditions when the craft is undergoing high gravational force stress (referred to as high-G stresses) and the pilot loses his control capabilities or consciousness and "blacks out".

BACKGROUND

In the case of a craft, such as high performance aircraft, control personnel such as the pilot or crew member are a limiting factor during flight. If cerebral dysfunction of such personnel were to occur and go undetected, the result could be catastrophic loss of life and/or property—not only involving the craft itself, but the surrounding environment should the craft go out of proper control. The extremely rapid performance characteristics of modern, high speed aircraft calls for almost instantaneous corrective control action to avert tragedy. Where a craft encounters hostile forces, temporary evasive action may be required of a degree accompanied by high-G stress where the pilot blacks out—temporarily. Here again almost instantaneous control action is required to conduct the desired evasive action. It may be desirable to have control either returned to the pilot following recovery from the black out, or the aircraft maneuvered to a desired status or destination.

Technology exists for monitoring selected characteristics of the human body in vivo. U.S. Pat. No. 4,281,645 describes embodiments of a device capable of "in vivo, in situ, non-invasive, atraumatic and continuous monitoring of three parameters of crucial significance related to organ metabolism' where "information on the state of circulatory adequacy and oxygen sufficiency are needed". Columns 11-14 of this patent describe details of the measurements of these metabolic parameters. Measurement of any one or any combination of these is useful in detecting pilot blackout and recovery from blackout. U.S. Pat. No. 4,380,240 issued to Frans F. Jobsis et al, there is described a spectrophotometric method directed to non-invasive, continuous, atraumatic, in vivo, in situ monitoring of metabolism in a body organ. It is generally known that metabolism and more particularly oxygen sufficiency and adequacy of utilization are parameters of fundamental importance in accessing the function of any body organ. This is made self-evident when one considers that the energy provision for tissue function is underwritten for better than 94 percent by oxidative reactions involving the reduction of $O_2$ to $H_2O$. In the absence of sufficient oxygen, this process becomes impaired with a corresponding impairment in organ function. In instances of extensive oxygen deprivation, over a period of time the organ loses viability and as a result the individual often has the same fate.

Although all organs are adversely affected by oxygen insufficiency, perhaps the problem is most acute in the case of the brain because of its exquisite sensitivity with respect to oxygen demand and its complete dependence on oxidative metabolism for proper function and viability. For example, an absence of adequate oxygen delivery by blood to the brain for more than a dozen seconds produces dysfunction and an absence for longer than a few minutes spells irreversible damage. A less acute impairment of oxygen availiability leads to a gradual loss in brain function, expecially with respect to the higher centers of the cerebral cortex.

The NIROscope is a known monitoring device which has been shown to provide accurate and immediate feedback with regard to the adequacy of cellular oxygention in the cerebral cortex. This device employs a solid-state laser, in the near-infrared spectrum and demonstrates on a heart beat to heart beat basis the level of cerebral functions as measured by oxygenation of the cytachrome c-oxidase. This enzyme system is the terminal component of the mitochondrial respiratory chain, and catalyzes greater than 95% of cellular oxygen consumption. Monitoring this enzyme provides early and accurate detection of oxygen delivery dysfunction on a cellular level, and has been shown to provide remarkable capabilities to detect brain dysfunction.

This enzyme system exhibits an absorption band betwee 800 and 900 nm, which is in the near infra-red spectrum. This band disappears when the enzyme system becomes reduced. Skin and bone are relatively transparent in this spectral region, and therefor monochromatic, or dichromatic laser radiation can be directed through intact skin and bone, and reflectance as well as absorbance can be calculated. Light from the laser is captured at the transmitting apparatus, located away from the subject. The light is delivered to the subject in two or more transmitting "optrodes" applied to the base of the skull, temporal region or frontal region. A receiving optrode is placed 4 to 6 cm lateral to the transmitting optrode. Absorbance of light in this wavelength is attributable to the cytochrome c-oxidase system. These calculations are accomplished using the Beer-Lambert Law. Corrections can be made electronically for absorbance due to hemoglobin. In view of the fact that this prior art has been discussed extensively in the patent literature and publications, for example (see U.S. Pat. Nos. 4,223,680, 4,281,645, 4,321,930, 4,380,240 and 4,510,938) such discussion will not be repeated here but the subject matter thereof is incorporated herein by reference. It is sufficient to state that a near infra-red oxygen sufficiency scope (NIRO-scope) exists and is employed to monitor the adequacy of oxygen delivery to brain tissue. Means are provided for securing to the brain, a light source housing and light detector housing used for monitoring metabolism.

In a preferred embodiment this apparatus is mounted on the pilots head under his helmet and the input and output signals are coupled by means of fiber optic cables to a light source and processing circuitry. See U.S. Pat. No. 4,510,938 issued to Frans F. Jobsis for a more detailed discussion of the considerations involved. It is sufficient for our purposes to state that this system or other similar sensing systems provide rapid detection of G-induced cerebral hypoxia, oxygen delivery hypoxia, or other pilot failure that would otherwise go undetected resulting in pilot/aircraft loss. Other less common problems such as pilot death, stroke, or injury due to foreign object damage would be detected. Non-high performance applications might include detection of hypoxia in high altitude transport due to oxygen failure or decompression.

Aircraft may be controlled manually or control may be transferred to an automatic control system in response to appropriate signals. For example, U.S. Pat. No. 3,337,163 describes an arrangement where control is immediately restored to the automatic flight control system whenever the pilot removes his hands from the manual control. Autopilots for maneuvering aircraft which can be locally or remotely engaged and disengaged for operation are known in the art.

SUMMARY

Briefly, in accordance with one embodiment of this invention, there is provided a method and apparatus for controlling an aircraft piloted in a first manner by a human being and undergoing high gravitational forces comprising the steps of monitoring said human being to detect the appearance of a given level of intolerable level of cerebral hypoxia or blackout due to such forces, responding to said detected given level to replace controlling said aircraft piloted in said first manner by said human being to controlling said aircraft in a second manner without piloting by said human being, and returning control of said aircraft for piloting by said human being in response to the return of a given tolerable level of cerebral hypoxia or recovery from blackout due to such forces.

Accordingly, an object of this invention is to enable desirable aircraft maneuvering following pilot blackout due to high-G forces.

Another object of this invention is to override human pilot control of an aircraft during pilot blackout and to enable resumption of pilot control following blackout disappearance.

Another object of this invention is to replace human pilot control of an aircraft which is limited above a first level of gravitational forces to automatic control which is limited by a higher level of gravitational forces, and returning to human pilot control following return to below said first level of gravitational forces.

Another object of this invention is to sense the oxygenation level in a human pilots brain during aircraft flight and shifting between pilot control and automated, non pilot control as a function of said sensed oxygenation levels and a desired flight maneuver.

A further object of this invention is to provide for improved craft maneuvering in response to a sensing of an undesirable metabolic condition of the craft operator.

BRIEF DESCRIPTION OF THE DRAWINGS

These as well as other objects and advantages of this invention will be better understood by careful study of the following detailed description of the presently preferred exemplary embodiment taken in conjunction with the accompanying drawings, of which.

DETAILED DESCRIPTION OF THE INVENTION

Figure 1:
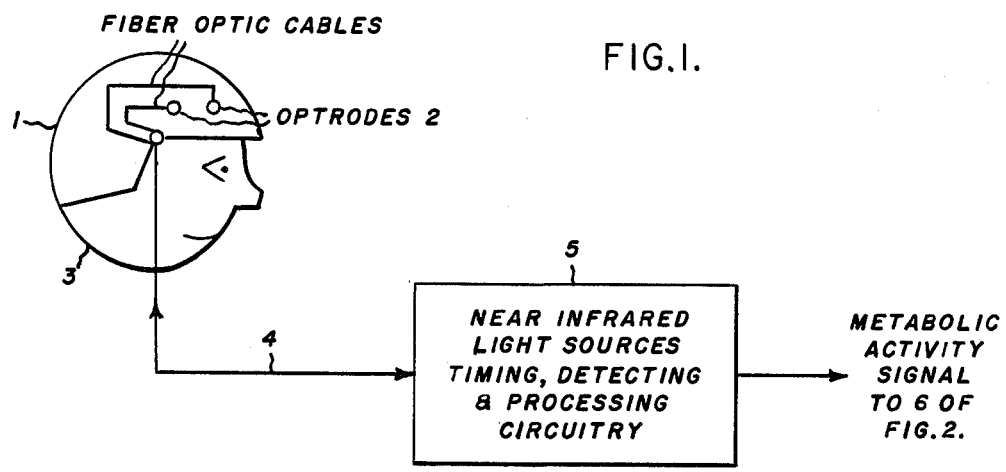
FIG. 1 is a schematic view of one manner of attaching a metabolism monitor to a selected portion of the human body, e.g. the brain, and providing input and output coupling between the brain and signal processing circuitry for providing a control signal indicative of substantially continuous and rapid measure of local metabolic oxygen dependent activity.

An exemplary embodiment of the metabolic sensor included in a pilot's helmet 1 is shown in FIG. 1. Here transmitting and receiving optrodes 2 are attached to the base of the skull of pilot 3 under his helmet 1. Fiber optics cable 4 provides at least one measuring and one reference wavelength of near infra red light from source 5 for application via an optrode 2 to the brain of the pilot. As mentioned in the previously referenced patents the frequency and coupling points to the brain are selected to indicate the absorption of the incident light, the extent of which is dependent upon a specific state of the metabolic, oxygen dependent activity of the selected brain portion. Light reflected directly back essentially from the selected point as well as light reflected and scattered from a point near the selected point to a second optrode are detected and returned by selected bundle of fibers in 4 to processor 5. The body mounted elements of FIG. 1 are used in association with near infra-red sources, timing, detecting and processing circuiting as well as measuring techniques described in the aforementioned patents, particularly U.S. Pat. No. 4,223,680. The output of processor 5 is a signal providing a substantially continuous and rapid measure of metabolic activity of pilot 3, such as the level of cerebral oxygenation.

Figure 2:
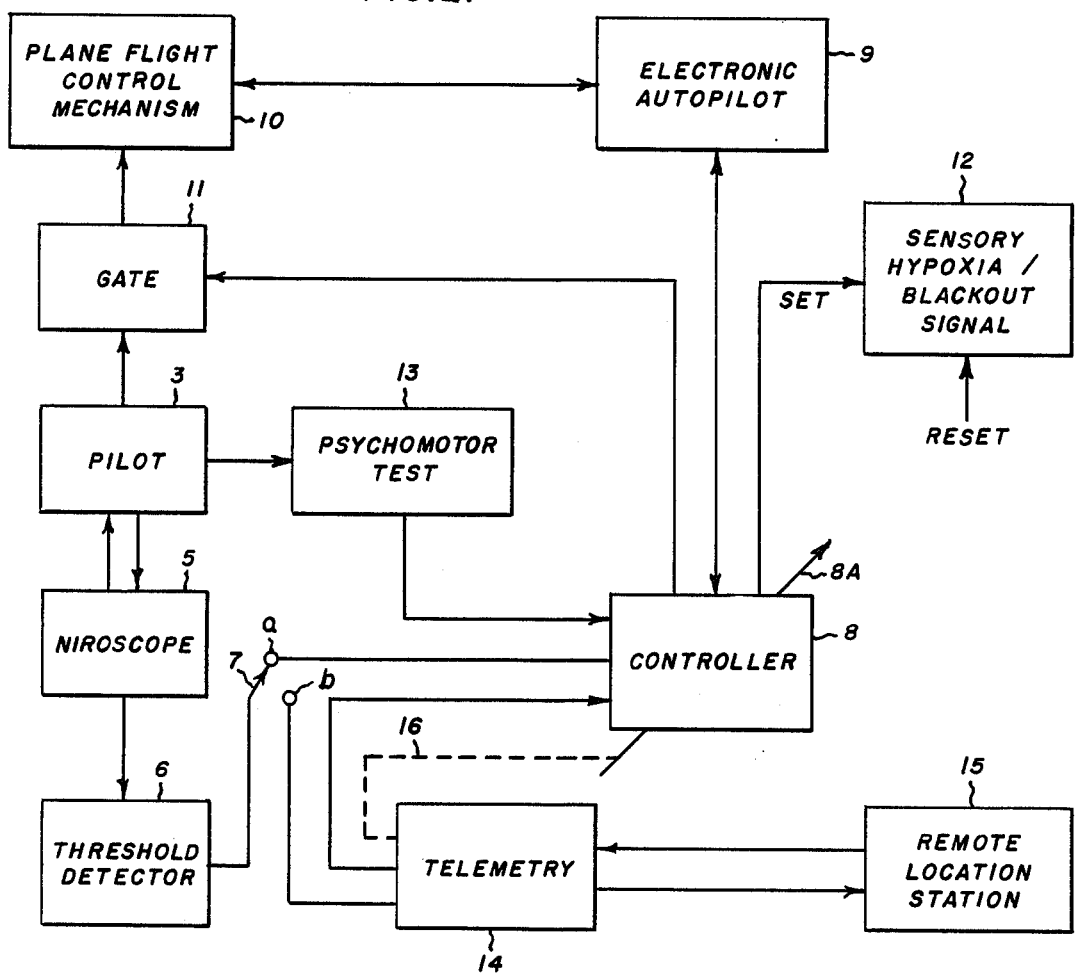
FIG. 2 is a block diagram of one embodiment of the invention wherein a pilot may elect to enable an airborne automatic pilot to take over control of the plane in response to a sensed predetermined metabolic condition of the pilot. Alternatively the controller can alert a remote station (ground or other craft) to enable the automatic pilot. The autopilot issues control signals to cause the plane to execute an automatic preprogrammed or remote station controlled flight maneuver or pattern. The pilot is given the option of resuming control os the plane's flight upon returning from blackout.

Referring to FIG. 2, there is shown one exemplary embodiment utilizing the control signals from 5 in the case where the pilot blacks out, as for example, because of high-G manuevers. Here, a blood oxygen delivery monitoring device, such as Niroscope 5, supplies a signal to black-out threshold detector 6. Detector 6 establishes a threshold signal level which when exceeded (indicating pilot black-out or serious or intolerable hypoxia) causes controller 8 via switch position 7a to engage automatic pilot 9. Automatic pilot 9 responds to controller 8 to issue control signals to the planes control mechanism 10 to cause the plane to execute an automatic programmed control of the planes flight. The particular programmed flight control can be selected by means of a selector depicted by arrow 8A. This could involve automatically taking the pilot to a safer altitude and/or attitute or other remedial course. Autopilots exist which can control an airplanes movements through a series of programmable, executed maneuvers with time. The programming is indicated by the arrow 8A. If it is necessary that the pilot avoid piloting the craft while fighing for consciousness on the threshold of blackout, controller 8 supplies a signal to Gate 11 which prohibits pilot control of control mechanism 10 until pilot consciousness is detected by controller 8. In this event, controller 8 signals the pilot by means of 12 that he has undergone a blackout. A blackout could have occurred without the pilots awareness. Device 12 may comprise a light or audible sound or other sensory indication to the pilot. To further insure that the pilot is fully capable of operating the aircraft, a psychomotor test circuit 13 is provided. This could simply involve pilot pressing of a series of buttons in the proper sequence to acknowledge pilot capability to controller 8. Controller 8 responds to a signal from 7 indicating that the pilot has recovered from serious hypoxia or blackout and an acceptability check by pilot operated psychomotor check 13 to open or unblock gate 11 permitting the pilot to resume aircraft flight control and to terminate control by autopilot 9.

If switch 7 is closed to the 7b position the blackout or non-blackout output signals are fed directly via controller 8 to Telemetry Device 14 (such as radio) for relaying to a remote location control 15 such as an aircraft ground controlled station or a second aircraft. Control 15 can then elect to send signals via Telemetry 14 back to controller 8 to disable pilot control by blocking gate 11 and controlling autopilot 9 to enable the execution of a predetermined or desired maneuver as previously described. Telemetry device 14 can select or modify the flight controlling signals in accordance with instructions from 15 as indicated by the dashed connection 16 to control 8A. Where in flight myocardial infarction, coma or death occurs, a ground based operator is notified through telemetry and the aircraft may be controlled to an area where landing or destruction of the aircraft can be accomplished with minimum risk to other humans or property.

Figure 3:
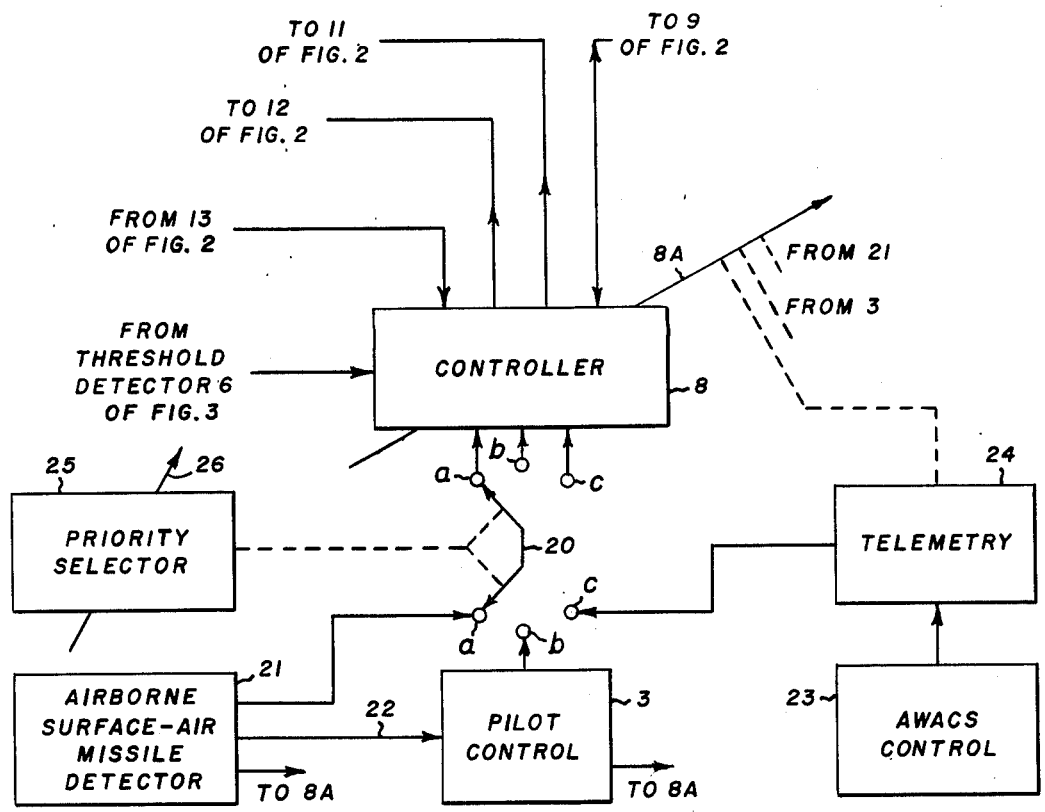
FIG. 3 is a block diagram of a further embodiment of the invention wherein control of the aircraft is removed from the pilot in response to local or remote detection of hostile activity against the aircraft in order to execute evasion maneuvers accomplished at high-G stress where pilot black-out may or does occur. Control of the aircraft is returned to the pilot once the sensors detect cerebral oxygenation when G-induced hypoxia is over.

FIG. 3 illustrates a further embodiment in which switch 20 in the position "a" shown permits an airborne surface missile detector 21 to enable controller 8 to initiate an evasive maneuver. For example, should an aircraft encounter a hostile force, the detector 14 aboard the aircraft or at an airborne AWAC control would, for example, detect the launching of surface to air missiles and initiate the evasive action. Alternatively, with the switch 20 in position b, the detector 14 would alert the pilot over coupling 22 to initiate the evasive maneuver. Also, in position 20c, detector 23 at a remote location, such as an AWACS aircraft or a ground station—upon detecting hostile action—could initiate evasive action through telemetry 24, such as radio, via controller 8. The selection of which mode of operation is desired can be established by a programmed priority selector 25 mounted on the aircraft which establishes priority among control by 21, 3 or 23 in accordance with a pilot control 26. If the aircraft is involved in a low altitude ground support mission, surface to air missile detection by 21 may be selected as first priority for controlling the evasive action, pilot control second and AWACS control third. If the aircraft is in reconnaissance mode, 23 may be selected to be first priority and 3 or 24 the second or third priority. If air to air combat is involved with the pilot being attacked by multiple sources, then 3 may become first priority and 23 the second priority. The maneuver or automatic evasion program triggered by 21, 3 or 23 enables the autopilot to respond to the selected program to take over control and accomplish evasion at high G-stress where the pilot may black out. Where a hostile force is not so equipped or capable, it is therefore unable to pursue or can be destroyed. In response to pilot blackout, controller 8 responds to the blackout signal from 6, as previously described, to block gate 11. After the evasive maneuver is executed, control of the aircraft may be returned to the pilot once the NIROSCOPE 5 signals cerebral oxygenation when serious G-induced hypoxia is over. Thus, following the execution of the maneuver or automatic evasion at high G-stress, and pilot monitoring by 5 indicates recovery from serious hypoxia or blackout, and an acceptability check by pilot operated device 13, controller 8 unblocks gate 11 permitting the pilot to resume aircraft flight control and terminates autopilot control.

The controller 8 which controls the operation of the Electronic Autopilot is in the exemplary embodiment a microprocessor based device. Insofar as the present invention is concerned, the microprocessor may be of conventional design except for the programmable flight control function which may be embodied in a suitable computer program of the type depicted in the flow chart of FIG. 4. As will be appreciated the controller 8 may be embodied as a separate sub-routine or embodied directly within other automatic pilot control program routines. Entry to the controller function occurs as a result of an interrupt signal or the like which may occur upon the receipt of a blackout signal from 6. In the absence of a blackout signal from 6, the controller 8 is in a first state. The sensory blackout signal device 12, which may be a colored light, is normally turned off, and the Gate 11 is in a first or unblocked state permitting pilot 3 to operate the plane flight control mechanism 10 manually. Upon receipt of a blackout signal from 6, controller 8 is activated to a second state, signal device 12 is set or turned on and gate 11 is set to a second state or blocked, thereby preventing the pilot 3 from operating the plane. In this second state, controller 8 controls Autopilot 9 in accordance with the preprogrammed flight pattern the pilot previously selected by 8A. This could involve automatically taking the pilot to a safer altitude and/or attitude, etc.

Upon recovery from blackout, a non-blackout signal causes controller 8 to return to its first state. In this state, controller 8 verifies the pilots metabolic condition by checking his passing the psychomotor test. If passed, controller 8 unblocks gate 11 permitting pilot manual control of the aircraft and terminates the autopilot control. The pilot resets the blackout signal manually upon resuming control.

Figure 4:
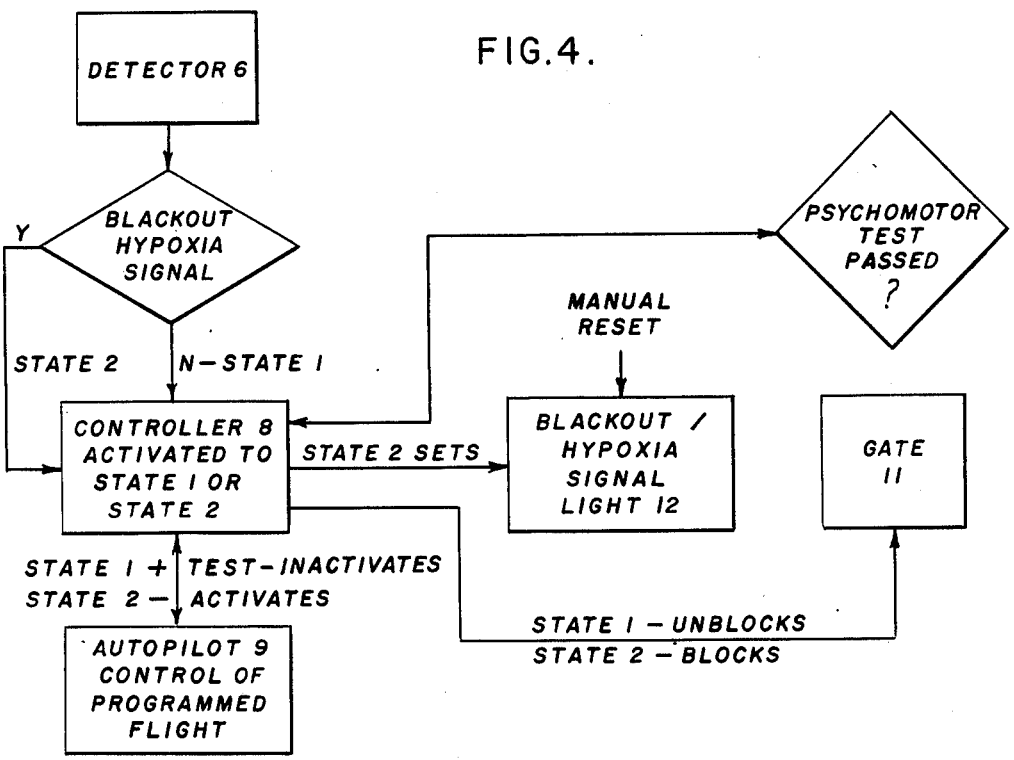
FIG. 4 is a flow diagram useful in explaining the invention as shown in FIG. 2.

The flow diagram for the embodiment of FIG. 3 would be similar to that shown in FIG. 4 except for controller 8 having additional inputs corresponding to the different scenarios represented by switch positions of 20 selected by selector 26 to execute selective preprogrammed or remote controlled programmed, evasive action drive of the auto pilot. Upon completion of the evasive action, the pilot could resume control of the craft provided he was free of serious hypoxia or blackout as demonstrated by the signal from 6 and verified by the signal from 13.

Although only one exemplary embodiment of the invention has been described in detail, those skilled in the art will recognize that many modifications and variations may be made in this embodiment while yet retaining many of the novel features and advantages of this invention. For example, while the exemplary embodiment of the invention has been described in terms of aircraft application—the invention may be applied to other situations such as decompression induced hypoxia, oxygen delivered failure induced hypoxia, etc.

involving diving craft, fire fighting equipment, etc. Accordingly, all such variations and modifications are intended to be included within the scope of the appended claims.

What is claimed is:

1. The process of controlling a craft capable of undergoing high-G forces which can cause a human pilot to undergo an intolerable level of cerebral hypoxia and lose control of piloting said craft along a first flight controlled path comprising, providing a source of a first signal representative of a need to change said first flight controlled path, providing a source of a second signal representative of a second flight controlled path, responding to said first and second signals to cause said craft to execute said second flight controlled path in place of said flight controlled path, at least one of said first or second signals involving a generation of high-G forces which may cause the pilot to undergo such intolerable level of cerebral hypoxia, monitoring the level of adequacy of oxygen delivery by blood to the brain of said pilot to provide a third signal representative of the tolerable or intolerable level of cerebral hypoxia and responding to a tolerable cerebral hypoxia level of said third signal for enabling said pilot to regain control of piloting of said craft.

2. A process according to claim 1 wherein said first signal is representative of a hostile condition likely to harm the craft and/or pilot.

3. A process according to claim 2 wherein said sources of said first and second signals are located on said craft.

4. A process according to claim 2 wherein said first signal source is remotely located and said second source is located in part on said craft and in part remotely located, and providing communications between the parts of said second source.

5. A process according to claim 1 wherein said first signal is representative of a hostile condition which is likely to harm the craft and/or pilot and said source of said first signal comprises a first source located on said craft and a second source located remotely of said craft, and selectively responding to said first signal from said first source or said second source in accordance with a selectable priority.

6. An arrangement for controlling a craft capable of undergoing high-G forces which can cause a human pilot to experience a level of cerebral hypoxia sufficient to lose control of piloting said craft along a first flight path controlled by said pilot comprising, means for monitoring the level of adequacy of oxygen delivery by blood to the brain of the pilot to provide a first signal representative thereof, means responsive to tolerable and intolerable levels of such adequacy of said first signal for enabling or disabling said pilot from piloting said craft comprising, a source of a second signal representative of a second flight controlled path, and means coupled to said source of second signal and responsive to an intolerable level of said first signal for disabling said pilot from piloting said craft and enabling said craft to execute said second flight controlled path in place of said first flight controlled path.

7. An arrangement according to claim 6 further comprising means responsive to a return to a tolerable level of said first signal for enabling said pilot to resume flight control of said flight.

8. An arrangement according to claim 7 wherein said last named means further comprises a pilot sensory indication.

9. An arrangement according to claim 7 wherein said last named means comprises means for testing the psychomotor efficiency of said pilot to provide an acceptability signal, and means responsive to said acceptability signal for enabling said pilot to resume flight control of said craft.

10. An arrangement according to claim 6 wherein said source of a second signal comprises a craft flight control mechanism, an autopilot comprising a source of stored second flight controlled path information, a threshold detector and a controller, said threshold detector responsive to said first signal for producing tolerable or intolerable level output signals, said controller responsive to said output signals indicating an intolerable level signal for activating siad autopilot, said flight control mechanism coupled to said activated autopilot and responsive to said stored second flight control path information for causing said plane to execute said second flight controlled path, said controller responsive to said output signals indicating a tolerable level signal for disabling said autopilot and enabling pilot control of said plane flight control mechanism.

11. An arrangement for controlling an aircraft capable of undergoing high-G forces which can cause a pilot to undergo cerebral hypoxia and become disabled from controlling said aircraft comprising means for sensing the level of adequacy of oxygen delivery by blood to a pilots brain to provide blackout and non-blackout signals, a source of signals representing a programmed flight control path involving the generation of high-G forces which may cause pilot blackout, means for enabling said source to cause said aircraft to execute said programmed flight control path, and means for disabling said source to permit return of pilot control of said aircraft comprising means responsive to said non-blackout signals and not to said blackout signals.

12. An arrangement according to claim 11 wherein said means for sensing comprises means for sensing the level of cellular oxygenation in the brain of said pilot, a pilot's helmet, a signal sensing portion mounted on said helmet, a means for coupling said signal sensing portion to a desired portion of the pilot's brain, a signal processing portion located remote from said helmet, and means for coupling said signal processing portion to said signal sensing portion.

13. An arrangement according to claim 11 wherein said means for sensing comprises a near infra red oxygen sufficiency sensor.

14. An arrangement for controlling movement of a craft wherein a human operator may undergo cerebral hypoxia and become disabled from normally controlling said craft comprising means coupled to the brain of said operator for sensing the level of cerebral hypoxia to provide tolerable and intolerable cerebral hypoxia level signals, a source of signals representing a programmed path of movement, means for enabling said source to cause said craft to execute said programmed path of movement in response to an intolerable signal, and means for disabling said source to permit return of operator control of said craft comprising means responsive to a tolerable signal.

15. An arrangement according to claim 14 wherein said craft is subject to high-G stress causing operator blackout, and said intolerable and tolerable signals comprise operator blackout and operator recovery from blackout signals, respectively.

16. An arrangement according to claim 15 wherein said means for disabling said source comprises means for verifying the operators metabolic condition, said last named means comprising means for checking the operator's ability to pass a psychomotor test.

17. An arrangement according to claim 15 further comprising means for detecting a hostile condition developing, and means responsive to said detecting means for causing said craft to take evasive action sufficient to cause said operator to temporarily suffer blackout and cause said means for sensing to provide an intolerable signal, and means responsive to completion of said evasive action and said sensing means providing a tolerable signal for returning control of said craft to said operator.

18. An arrangement according to claim 14 wherein said craft is subject to high-G stress capable of producing high-G induced cerebral hypoxia and said means for sensing the level of cerebral hypoxia comprises means for sensing the adequacy of blood being delivered to the brain of said operator during such high-G stress.

19. The process of controlling a craft wherein a human pilot may undergo cerebral hypoxia and lose control of piloting said craft along a first flight controlled path comprising, providing a source of a first signal representative of a need to change said first flight controlled path, providing a source of a second signal representative of a second flight controlled path, responding to said first and second signals to cause said craft to execute said second flight controlled path in place of said first flight controlled path, monitoring the level of adequacy of oxygen delivery by blood to the brain of said pilot to provide a third signal representative thereof, said first signal comprising an undesired level of said third signal, and responding to a desired level of said third signal for enabling said pilot to regain control of piloting of said craft

* * * * *